(12) United States Patent
Seago

(10) Patent No.: US 9,737,340 B1
(45) Date of Patent: Aug. 22, 2017

(54) ADJUSTABLE ILIAC CONNECTOR

(71) Applicant: NuVasive, Inc., San Diego, CA (US)

(72) Inventor: Jeffrey M. Seago, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 27 days.

(21) Appl. No.: 14/856,467

(22) Filed: Sep. 16, 2015

Related U.S. Application Data

(60) Provisional application No. 62/051,206, filed on Sep. 16, 2014.

(51) Int. Cl.
*A61B 17/70* (2006.01)

(52) U.S. Cl.
CPC ...... *A61B 17/7041* (2013.01); *A61B 17/7002* (2013.01); *A61B 17/7032* (2013.01); *A61B 17/7037* (2013.01)

(58) Field of Classification Search
CPC ............ A61B 17/7041; A61B 17/7002; A61B 17/7032; A61B 17/7037
USPC ........ 606/246, 250–253, 256, 262, 267–270, 606/278, 279
See application file for complete search history.

(56) References Cited

U.S. PATENT DOCUMENTS

| | | | |
|---|---|---|---|
| 2,393,694 A | 1/1946 | Kirschner | |
| 5,176,680 A | 1/1993 | Vignaud et al. | |
| 5,474,551 A | 12/1995 | Finn et al. | |
| 5,591,165 A | 1/1997 | Jackson | |
| 5,624,442 A | 4/1997 | Mellinger et al. | |
| 5,752,957 A | 5/1998 | Ralph et al. | |
| 6,520,990 B1 | 2/2003 | Ray | |
| 6,872,208 B1 | 3/2005 | McBride et al. | |
| 6,887,241 B1 | 5/2005 | McBride et al. | |
| 8,430,914 B2 * | 4/2013 | Spratt | A61B 17/7037 606/265 |
| 8,668,721 B2 | 3/2014 | Miller | |
| 9,060,815 B1 * | 6/2015 | Gustine | A61B 17/705 |
| 2002/0143330 A1 | 10/2002 | Shluzas | |
| 2004/0116928 A1 | 6/2004 | Young et al. | |
| 2004/0133202 A1 | 7/2004 | Suzuki et al. | |
| 2006/0106382 A1 | 5/2006 | Gournay et al. | |
| 2008/0021454 A1 | 1/2008 | Chao et al. | |
| 2008/0021455 A1 | 1/2008 | Chao et al. | |
| 2008/0021456 A1 | 1/2008 | Gupta et al. | |
| 2013/0211457 A1 | 8/2013 | Dickinson et al. | |
| 2013/0304128 A1 | 11/2013 | Lange et al. | |
| 2014/0277146 A1 * | 9/2014 | Li | A61B 17/7052 606/252 |

* cited by examiner

*Primary Examiner* — Pedro Philogene
*Assistant Examiner* — David C Comstock
(74) *Attorney, Agent, or Firm* — Bradley Arant Boult Cummings; Rory Schermerhorn

(57) ABSTRACT

An adjustable offset connector for connecting iliac screws to fixation rods. The connector includes an adjustable offset rod to facilitate mating the rod with the tulip of the iliac screws and an anti-torque mechanism designed to resist torque and securely lock the offset rod in position and provide a strong, stable connection.

13 Claims, 5 Drawing Sheets

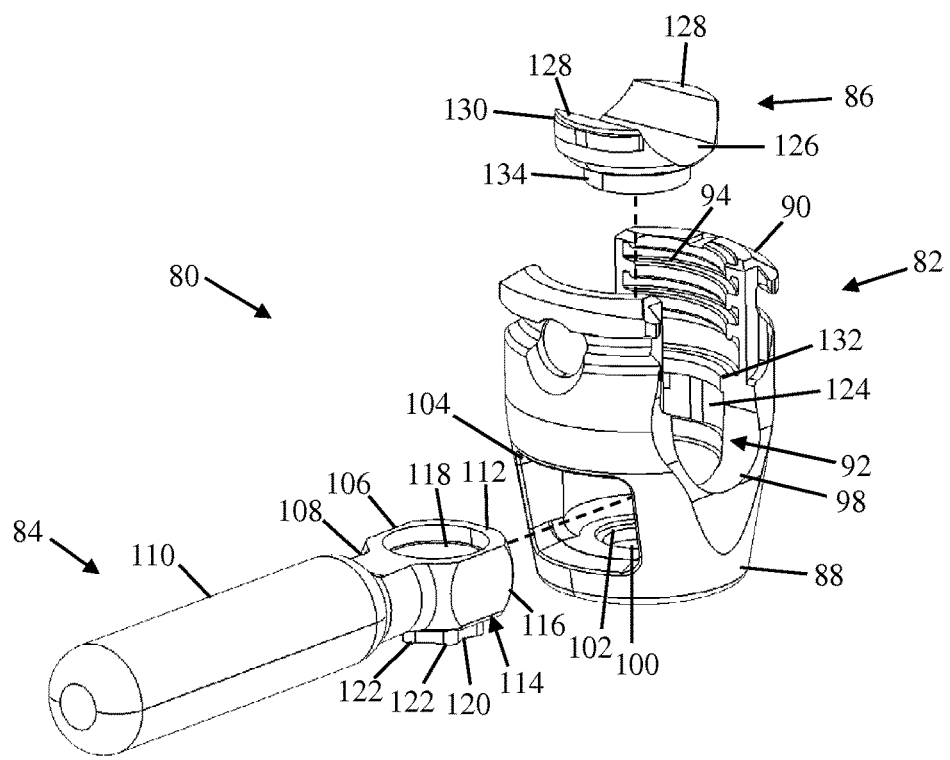
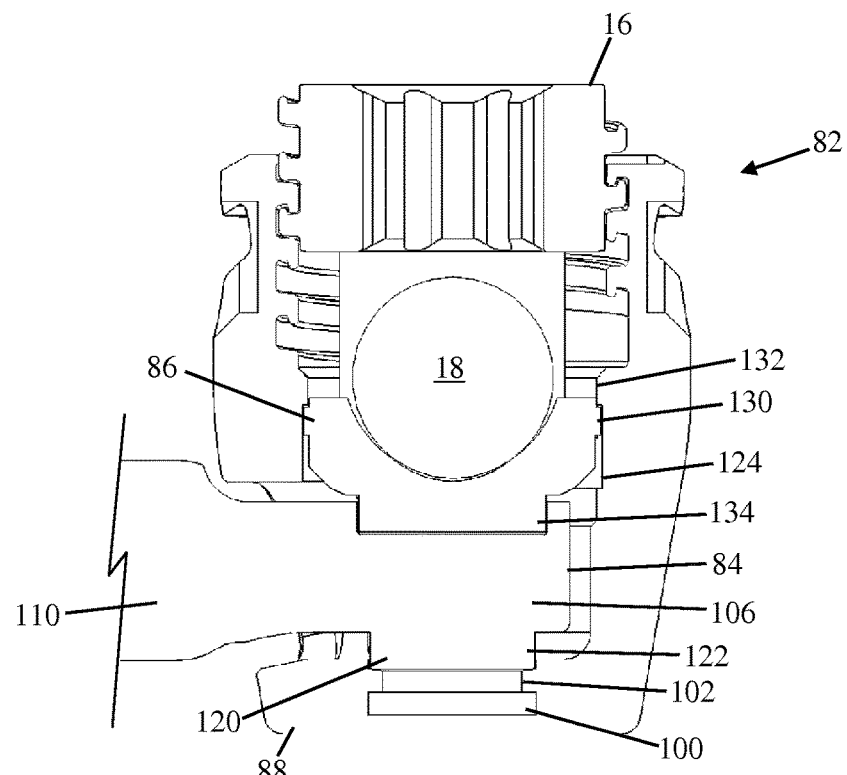
Fig. 8
Fig. 9

ADJUSTABLE ILIAC CONNECTOR

CROSS-REFERENCES TO RELATED APPLICATIONS

This application is a non-provisional application claiming the benefit of priority under 35 U.S.C. 119(e) from U.S. Provisional Patent Application Ser. No. 62/051,206 filed on Sep. 16, 2014, the entire contents of which is hereby expressly incorporated by reference into this disclosure as if set forth in its entirety herein.

FIELD

This disclosure relates to spinal fixation connectors for use with a spinal fixation constructs.

BACKGROUND

During certain spinal fixation procedures, for example, an open spinal deformity procedure, the surgeon may choose to connect the main fixation rod construct of the lumbar spine to the pelvis. To do so, the surgeon will place screws through the ilium, and then connect the iliac screws to the rod from the lumbar spine with an iliac offset connector. Iliac connectors tend to resemble a tulip with a rod extending off one of the faces. This offset rod extends laterally toward the ilium and mates with the rod slot of the iliac screw. Most iliac connectors introduced to date are fixed, that is, the rod extends outward from the tulip in a fixed angle. The fixed nature of the rod from the connector can often make it difficult to achieve optimum mating alignment with the iliac screw. To facilitate alignment connection and reduce alignment issues connectors with an adjustable angle rod have been attempted. However, the joints used to provide adjustability introduce more weakness into the connection than is generally desirable in an area and application that incurs high loads. The present device is directed at alleviating or reducing these concerns.

SUMMARY

An adjustable offset connector is described for connecting iliac screws to fixation rods. The connector includes an adjustable offset rod to facilitate mating the rod with the tulip of the iliac screws and an anti-torque mechanism designed to resist torque and securely lock the offset rod in position and provide a strong, stable connection. The anti-torque mechanism includes a geometric extension on the underside the offset rod and/or load ring that sits in the tulip between the offset rod and the main construct rod. Receptacles in the tulip and/or in the top side of the offset rod receive the geometric extensions on the underside of the offset rod and load ring, respectively. Lips situated in the receptacles interact with the geometric extensions upon tightening to resist torque. Prior to final tightening, the offset rod is able to pivot with infinite variability within the limits of the tulip. Upon final tightening, the geometric extensions shear through portions of the lips. The shearing results in the interdigitation of the geometric extensions and lips, which enhances resistance to torque.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 8 is an exploded perspective view of another example of an offset connector forming part of the spinal fixation construct of FIG. 1;

FIG. 9 is a sectional view of the offset connector of FIG. 8 in an unlocked position;

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The adjustable iliac connector disclosed herein boasts a variety of inventive features and components that warrant patent protection, both individually and in combination.

Figure 1:
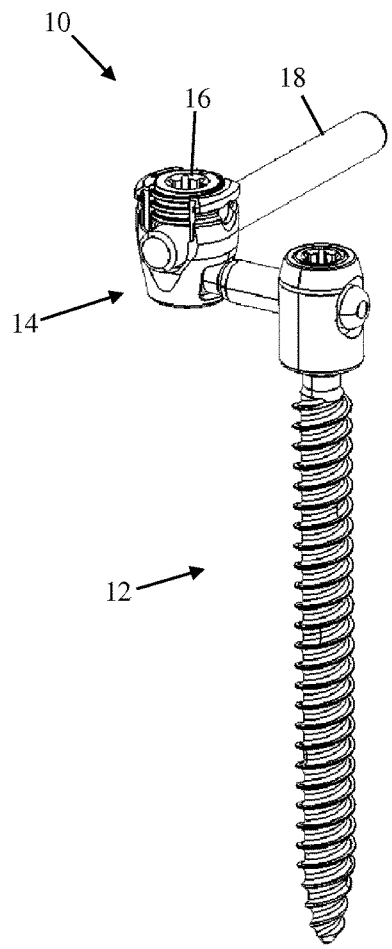
FIG. 1 is a perspective view of an illiac portion of a spinal fixation construct according to one example embodiment.
Figure 2:
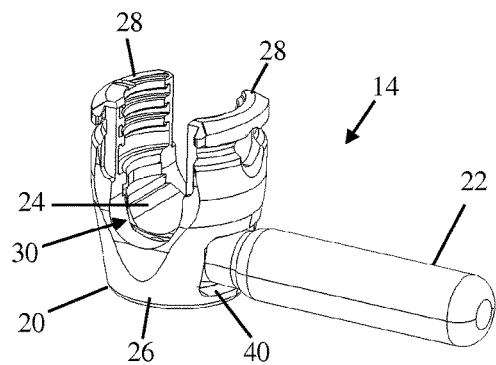
FIG. 2 is a perspective view of one example embodiment of an offset connector forming part of the spinal fixation construct of FIG. 1.
Figure 3:
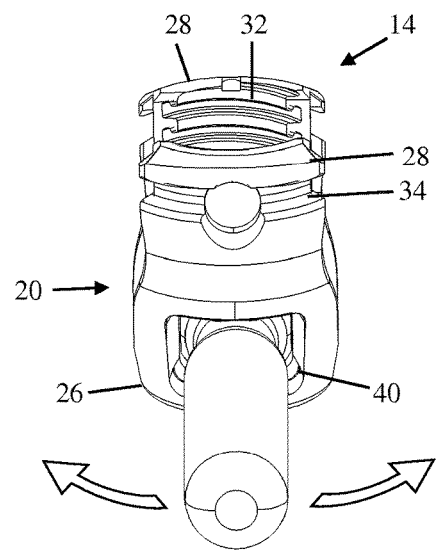
FIG. 3 is another perspective view of the offset connector of FIG. 2.
Figure 4:
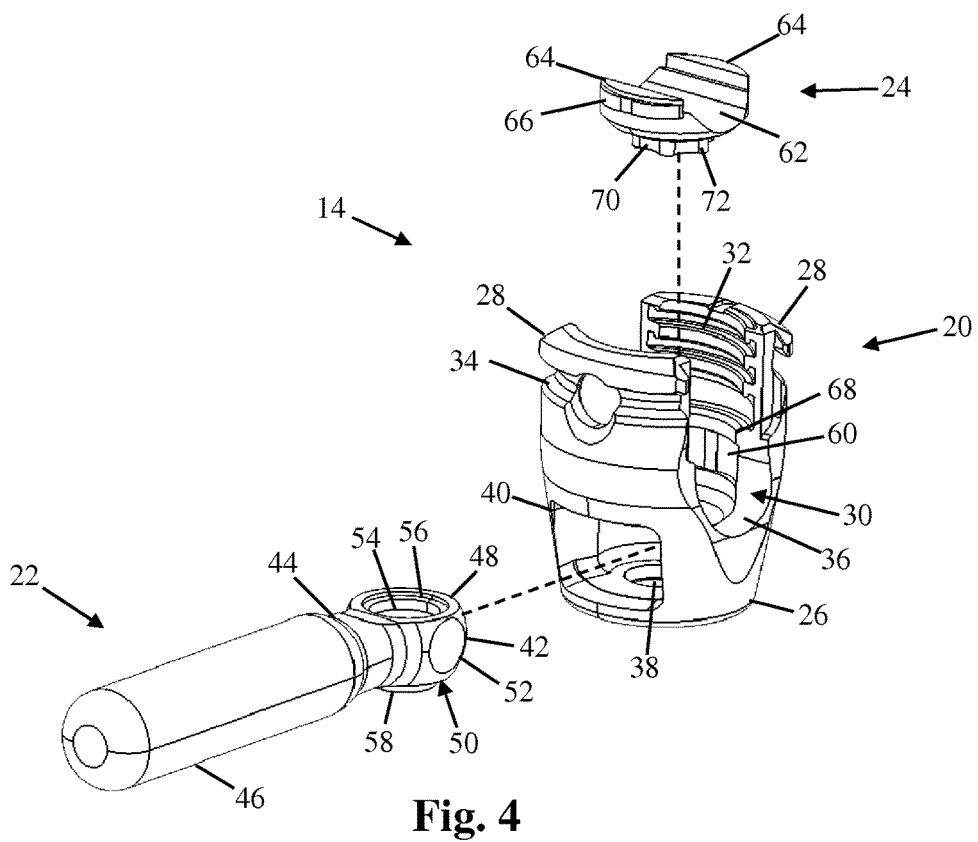
FIG. 4 is an exploded perspective view of the offset connector of FIG. 2.

FIG. 1 illustrates an example of a spinal fixation construct 10 that constitutes a portion of a larger multi-level spinal construct (not shown). The spinal fixation construct 10 includes an iliac screw 12, an offset connector 14, a setscrew 16, and a spinal rod 18. When spinal fusion surgery is performed using a posterior approach (spine is accessed from the posterior direction), the surgeon may choose to provide fixation between the lumbar spine and the pelvis. To do so, the surgeon can place the iliac screws 12 through the ilium as a bone anchor and then use a connector 14 that connects the iliac screw 12 to the spinal rod 18 extending from the lumbar spine. In order to accommodate the anatomy of the pelvis, the connector 14 is offset. As will be described in further detail below, the offset connector 14 of the present disclosure is an adjustable offset connector 14 that has a moveable connector rod 22 that allows the surgeon to find the optimal fit between the spinal rod 18 and the iliac screw 12.

FIGS. 2-7 illustrate a first example of an adjustable offset connector 14 according to one embodiment. By way of example only, the adjustable offset connector 14 of the present disclosure includes a tulip 20, a connector rod 22, and a load ring 24. The tulip includes a base 26 and a pair of upstanding arms 28 separated by a rod channel 30. The inner faces of the upstanding arms 28 include a guide and advancement feature region 32 that enables mating engagement between the tulip 20 and the setscrew 16 having a complementary guide and advancement feature. The outer face of each of the upstanding arms includes a perimeter recess 34 configured to receive a portion of another surgical instrument, for example an inserter and/or rod guide (not shown). Each end of the rod channel 30 includes a generally arcuate surface 36 formed with portions of each of the upstanding arms 28 and the base 26 to provide a generally U-shape to rod channel 30. The base 26 includes an annular recess 38 formed in the general middle of the inner surface of the base 26 and a lateral aperture 40 formed through one of the sidewalls of the base 26. The annular recess 38 is configured to receive the post 58 of the connector rod 22, and enables pivoting of the connector rod 22 prior to final tightening. The lateral aperture 40 comprises a window through which the connector rod 22 extends from the inner portion of the tulip 20 to the iliac screw 12. The lateral aperture 40 shown by way of example in the accompanying figures has a generally rectangular perimeter shape, although other shapes possible within the scope of the disclosure. According to this example, the lateral aperture is sized and dimensioned to allow pivoting of the connector rod 22 up to 15° in either direction, though it will be appreciated that the aperture dimension can be modified to increase or decrease the degree of angulation permitted. The edges of the lateral aperture 40 provide a physical limitation to the degree of pivot that the construct allows.

The connector rod 22 includes a head 42, a neck 44, and a rod member 46. The head 42 has a generally circular perimeter shape, and further has a superior face 48, an inferior face 50, and a generally spherical outer surface 52 extending between the superior and interior faces. The superior face 48 includes a receptacle 54 formed therein configured to receive the shaped post 70 of the load ring 24. The receptacle 54 includes a circumferential lip 56 extending into the opening of the receptacle that effectively reduces the diameter of the receptacle 54. As will be explained, the lip 56 interacts with the shaped post 70 of the load ring 24 to resist torque and prevent the connector rod 22 from moving upon final tightening of the construct. The inferior face 50 has a post 58 extending therefrom. The post 58 of the instant embodiment is generally cylindrical in shape and has a smooth outer surface. The post 58 is further configured to nest within the annular recess 38 of the tulip 20. The smooth outer surface enables the post 58 to rotate within the annular recess 38 as the connector rod 22 pivots. The neck 44 connects the head 42 to the rod portion 46 and has a reduced diameter relative to the rod portion 46. The neck 44 has a diameter dimension that is slightly smaller than the height dimension of the lateral aperture 40 of the tulip 20 so that the neck 44 is able to move within the lateral aperture 40 prior to final tightening of the connector. The rod portion 46 is generally cylindrical and extends laterally from the neck 44. The rod portion 46 is configured to engage the iliac screw 12 and may be provided in any size necessary to span the distance between the iliac screw 12 and the tulip 20 (and therefore the spinal rod 18).

The load ring 24 is configured to nest within a recess 60 of the base 26 of the tulip 20 and has a superior facing generally arcuate surface 62 that forms a rod seat configured to receive and seat the spinal rod. The load ring 24 further includes a pair of arms 64 on either side of the arcuate surface 62. The outer face of the arms 64 each includes a ledge 66 that engages with an overhang 68 at the upper end of the recess 60. The interaction between the ledge 66 and the overhang 68 prevents egress of the load ring 24 from recess 60. The load ring 24 further includes a shaped post 70 extending inferiorly from the load ring 24. The shaped post 70 includes a plurality of gear-like teeth 72 positioned circumferentially around the post 70. In the example shown and described herein, the post 70 includes six gear-like teeth 72, however other configurations or more or fewer teeth are possible. The load ring 24 is able to translate within the recess 60, for example between a raised position and a lowered position.

Figure 5:
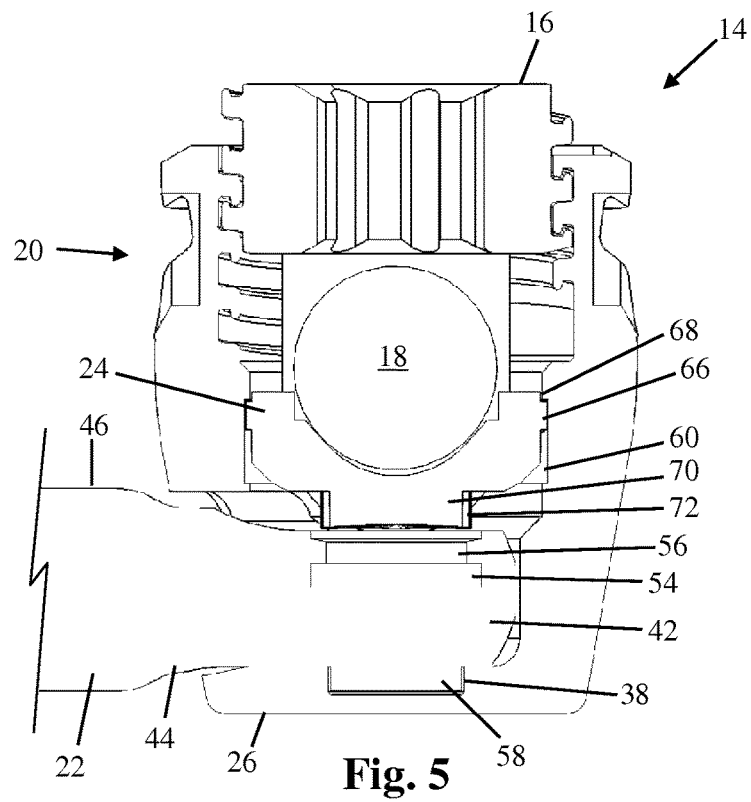
FIG. 5 is a sectional view of the offset connector of FIG. 2 in an unlocked position.
Figure 6:
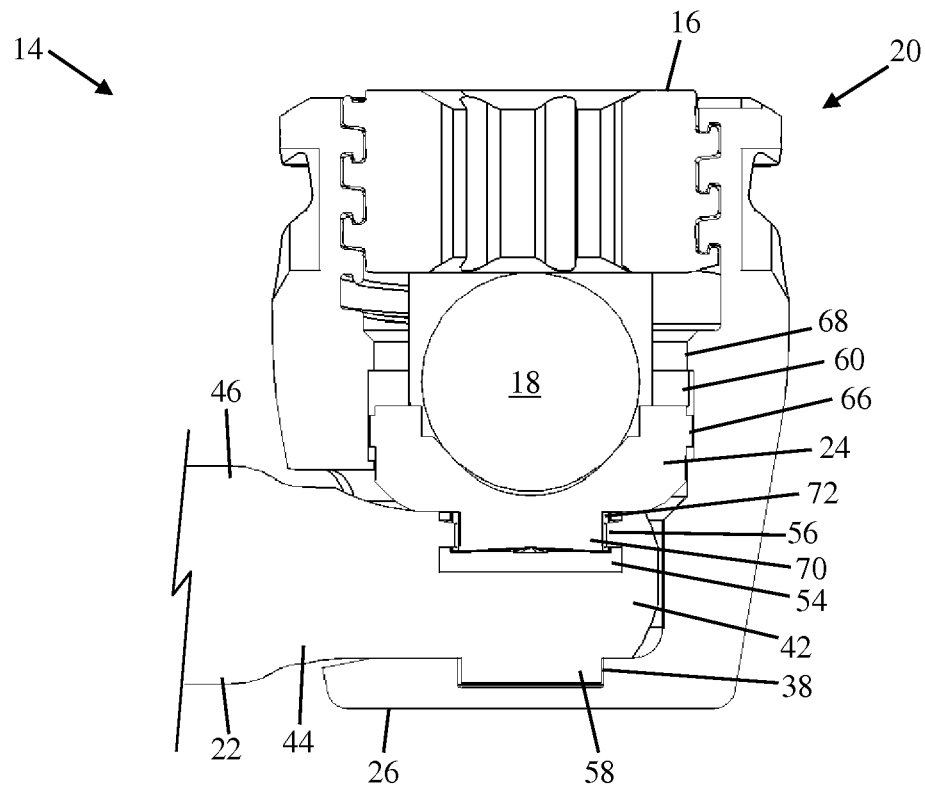
FIG. 6 is a sectional view of the offset connector of FIG. 2 in a locked position.
Figure 7:
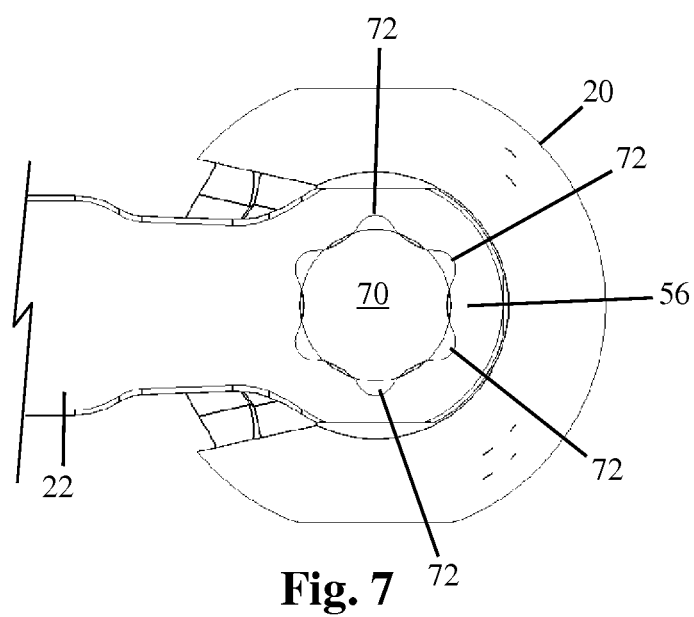
FIG. 7 is a different sectional view of the offset connector of FIG. 2 in a locked position.
Figure 10:
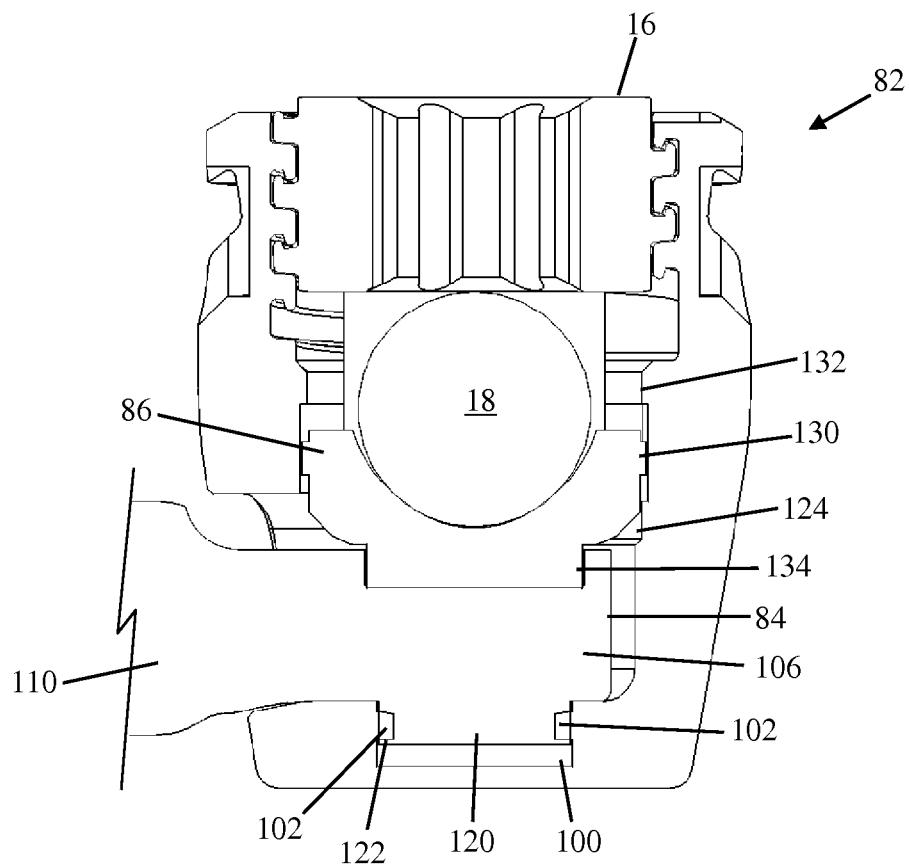
FIG. 10 is a sectional view of the offset connector of FIG. 8 in a locked position.
Figure 11:
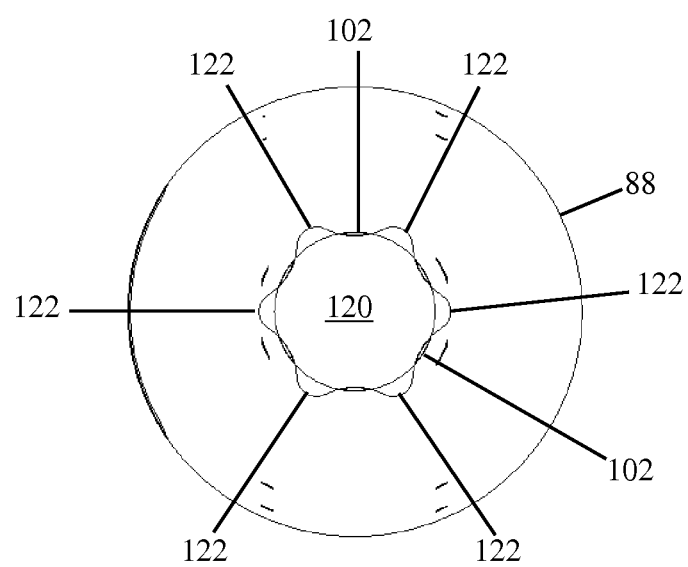
FIG. 11 is a different sectional view of the offset connector of FIG. 8 in a locked position.

In use, the offset connector 14 is provided with the load ring 24 in an initial raised position (e.g., FIG. 5). While the load ring 24 is in the raised position, the connector rod 22 is free to pivot within the tulip 20, and thus the positioning of offset connector 14 is adjustable by the surgeon. Once the surgeon finds the optimal position for the connector rod 22, the connector rod 22 can be locked in place by rotating the setscrew 16 within the tulip 20. This exerts a downward axial force upon the spinal rod 18, which in turn exerts a downward axial force upon the load ring 24. Upon final tightening of the construct, the load ring 24 is urged from the raised position to the lowered position (e.g. FIG. 6), with an axial force great enough to cause the gear-like teeth 72 to shear through the circumferential lip 56 of the receptacle 54 of the connector rod 22. Material in the shape of the gear-like teeth 72 gets removed from the circumferential lip 56, and the gear-like teeth 72 occupy the space of the removed material. This interdigitation of the circumferential lip 56 and gear-like teeth 72 (FIG. 7) locks the connector rod 22 in place and provides added torsional resistance to withstand the high loads that can occur in the iliac region of a fixation construct.

FIGS. 8-11 illustrate a second example of an adjustable offset connector 80 according to an alternative embodiment. By way of example only, the adjustable offset connector 80 of the present disclosure includes a tulip 82, a connector rod 84, and a load ring 86. The tulip includes a base 88 and a pair of upstanding arms 90 separated by a rod channel 92. The inner faces of the upstanding arms 90 include a guide and advancement feature region 94 that enables mating engagement between the tulip 82 and the setscrew 16 having a complementary guide and advancement feature. The outer face of each of the upstanding arms 90 includes a perimeter recess 96 configured to receive a portion of another surgical instrument, for example an inserter and/or rod guide (not shown). Each end of the rod channel 92 includes a generally arcuate surface 98 formed with portions of each of the upstanding arms 90 and the base 88 to provide a generally U-shape to rod channel 92. The base 88 includes a receptacle 100 formed therein configured to receive the shaped post 120 of the connector rod 84. The receptacle 100 includes a circumferential lip 102 extending into the opening of the receptacle that effectively reduces the diameter of the receptacle 100. As will be explained, the lip 102 interacts with the shaped post 120 of the connector rod 84 to resist torque and prevent the connector rod 84 from moving upon final tightening of the construct. The base 88 further includes a lateral aperture 104 formed through one of the sidewalls of the base 88. The lateral aperture 104 comprises a window through which the connector rod 84 extends from the inner portion of the tulip 82 to the iliac screw 12. The lateral aperture 104 shown by way of example in the accompanying figures has a generally rectangular perimeter shape, although other shapes possible within the scope of the disclosure.

According to the example shown, the lateral aperture is sized and dimensioned to allow pivoting of the connector rod 84 up to 15° in either direction. The edges of the lateral aperture 104 provide a physical limitation to the degree of pivot that the construct allows.

The connector rod 84 includes a head 106, a neck 108, and a rod member 110. The head 106 has a generally circular perimeter shape, and further has a superior face 112, an inferior face 114, and a generally spherical outer surface 116 extending between the superior and interior faces. The superior face 112 includes an annular recess 118 formed in the general middle of the superior face 112. The annular recess 118 is configured to receive the post 134 of the load ring 86, and enables pivoting of the connector rod 84 prior to final tightening. The inferior face 114 has a shaped post 120 extending inferiorly therefrom. The shaped post 120 includes a plurality of gear-like teeth 122 positioned circumferentially around the post 120. In the example shown and described herein, the post 120 includes six gear-like teeth 122, however other configurations or more or fewer teeth are possible. The neck 108 is connects the head 106 to the rod portion 110 and has a reduced diameter relative to the rod portion 110. The neck 108 has a diameter dimension that is slightly smaller than the height dimension of the lateral aperture 104 of the tulip 82 so that the neck 108 is able to move within the lateral aperture 104 prior to final tightening of the construct. The rod portion 110 is generally cylindrical and extends laterally from the neck 108. The rod portion 110 is configured to engage the iliac screw 12 and may be provided in any size necessary to span the distance between the iliac screw 12 and the tulip 82 (and therefore the spinal rod 18).

The load ring 86 is configured to nest within a recess 124 of the base 88 of the tulip 82 and has a superior facing generally arcuate surface 126 that forms a rod seat 98 configured to receive and seat the spinal rod. The load ring 86 further includes a pair of arms 128 on either side of the arcuate surface 126. The outer face of the arms 128 each includes a ledge 130 that engages with an overhang 132 at the upper end of the recess 124. The interaction between the ledge 130 and the overhang 132 prevents egress of the load ring 86 from recess 124. The load ring 86 further includes a post 134 extending therefrom. The post 134 of the instant embodiment is generally cylindrical in shape and has a smooth outer surface. The post 134 is further configured to nest within the annular recess 118 of the tulip connector rod 84. The smooth outer surface enables the annular recess 118 to rotate about the post 134 as the connector rod 84 pivots. The load ring 86 is able to translate within the recess 124, for example between a raised position and a lowered position.

In use, the offset connector 80 is provided with the load ring 86 in an initial raised position (e.g., FIG. 9). While the load ring 86 is in the raised position, the connector rod 84 is free to pivot within the tulip 82, and thus the positioning of offset connector 80 is adjustable by the surgeon. Once the surgeon finds the optimal position for the connector rod 80, the connector rod 84 can be locking in place by rotating the setscrew 16 within the tulip 82. This exerts a downward axial force upon the spinal rod 18, which in turn exerts a downward axial force upon the load ring 86, which in turn exerts a downward axial force upon the head 106 of the connector rod 84. Upon final tightening of the construct, the load ring 86 is urged from the raised position to the lowered position (e.g. FIG. 10), with an axial force great enough to cause the gear-like teeth 122 on the head 106 of the connector rod 84 to shear through the circumferential lip 102 of the receptacle 100 of the tulip 82. Material in the shape of the gear-like teeth 122 gets removed from the circumferential lip 102, and the gear-like teeth 122 occupy the space of the removed material. This interdigitation of the circumferential lip 102 and gear-like teeth 122 (FIG. 11) locks the connector rod 84 in place and provides the necessary torsional resistance for spinal fixation.

While the inventive features described herein have been described in terms of a preferred embodiment for achieving the objectives, it will be appreciated by those skilled in the art that variations may be accomplished in view of these teachings without deviating from the spirit or scope of the invention. Also, while this invention has been described according to a preferred use in spinal applications, it will be appreciated that it may be applied to various other uses desiring surgical fixation.

What is claimed is:

1. An adjustable offset connector for use with a spinal fixation system having an elongated cylindrical spinal rod and a plurality of bone anchor elements, at least one of the bone anchor elements including an elongated threaded shaft for gaining purchase within a vertebra and a head element positioned proximally from the shaft, the head element including a rod slot, the adjustable offset connector comprising:
   a housing element having an inner cavity and a pair of upstanding arms separated by a rod channel, the housing element further having a lateral aperture formed within the housing underneath one of the upstanding arms and an annular recess formed within a bottom surface of the inner cavity;
   a rod connector extending through the lateral aperture, the rod connector having a first end positioned within the inner cavity of the housing element and a second end configured to engage the rod slot of the bone anchor element to connect the housing element to the anchor element, the first end having a receptacle formed within a superior aspect and a cylindrical post extending from an inferior aspect, the cylindrical post configured to pivotably nest within the annular recess;
   a load ring positioned within the housing element between the inner cavity and the rod channel, the load ring having a superior facing surface configured to engage the spinal rod and an inferior facing surface including a shaped post, the shaped post having a plurality of gear-like teeth positioned around the perimeter of the shaped post;
   a setscrew configured to mate with the upstanding arms, the setscrew being advanceable to a locked position to effect compression of the offset connector by exerting an axial force on the spinal rod and load ring sufficient to cause the gear-like teeth of the shaped post to shear through a least a portion of the receptacle to create an interdigitation of the gear-like teeth and receptacle to prevent further movement of the rod connector.

2. The adjustable offset connector of claim 1, wherein the receptacle includes an annular lip overhang.

3. The adjustable offset connector of claim 2, wherein gear-like teeth of the shaped post shear through one or more portions of the annular lip overhang.

4. The adjustable offset connector of claim 1, wherein the lateral aperture is configured to allow the rod connector to pivot up to 15° in either direction prior to advancement of the set screw to the locked position.

5. An adjustable offset connector for use with a spinal fixation system having an elongated cylindrical spinal rod and a plurality of bone anchor elements, at least one of the bone anchor elements including an elongated threaded shaft for gaining purchase within a vertebra and a head element positioned proximally from the shaft, the head element including a rod slot, the adjustable offset connector comprising:
- a housing element having an inner cavity and a pair of upstanding arms separated by a rod channel, the housing element further having a lateral aperture formed within the housing underneath one of the upstanding arms and a receptacle formed within a bottom surface of the inner cavity;
- a rod connector extending through the lateral aperture, the rod connector having a first end positioned within the inner cavity of the housing element and a second end configured to engage the rod slot of the bone anchor element to connect the housing element to the anchor element, the first end having an annular recess formed within a superior aspect and a shaped post extending from an inferior aspect, the shaped post having a plurality of gear-like teeth positioned around the perimeter of the shaped post;
- a load ring positioned within the housing element between the inner cavity and the rod channel, the load ring having a superior facing surface configured to engage the spinal rod and an inferior facing surface including a cylindrical post, the cylindrical post configured to pivotably nest within the annular recess;
- set screw configured to mate with the upstanding arms, the set screw being advanceable to effect compression of the offset connector by exerting an axial force on the spinal rod, load ring, and first end of the rod connector sufficient to cause the gear-like teeth of the shaped post to shear through a least a portion of the receptacle to prevent further movement of the rod connector.

6. The adjustable offset connector of claim 5, wherein the receptacle includes an annular lip overhang.

7. The adjustable offset connector of claim 6, wherein gear-like teeth of the shaped post shear through one or more portions of the annular lip overhang.

8. The adjustable offset connector of claim 7, wherein the lateral aperture is configured to allow the rod connector to pivot up to 15° in either direction prior to advancement of the set screw to the locked position.

9. A method for facilitating the connection of a spinal rod and a bone anchor placed within a target bone, comprising:
- implanting a bone anchor in a portion of the target bone, the bone anchor including an elongated threaded shaft for gaining purchase within a vertebra and a head element positioned proximally from the shaft, the head element including a rod receiving element;
- positioning the spinal rod along a posterior aspect of the spinal column;
- connecting the spinal rod to the bone anchor with an adjustable offset connector, the adjustable offset connector comprising:
  - a housing element having an inner cavity and a pair of upstanding arms separated by a rod channel, the housing element further having a lateral aperture formed within the housing underneath one of the upstanding arms and an annular recess formed within a bottom surface of the inner cavity;
  - a rod connector extending through the lateral aperture, the rod connector having a first end positioned within the inner cavity of the housing element and a second end configured to engage the rod slot of the bone anchor element to connect the housing element to the anchor element, the first end having a receptacle formed within a superior aspect and a cylindrical post extending from an inferior aspect, the cylindrical post configured to pivotably nest within the annular recess;
  - a load ring positioned within the housing element between the inner cavity and the rod channel, the load ring having a superior facing surface configured to engage the spinal rod and an inferior facing surface including a shaped post, the shaped post having a plurality of gear-like teeth positioned around the perimeter of the shaped post;
  - a setscrew configured to mate with the upstanding arms, the setscrew being advanceable to a locked position to effect compression of the offset connector by exerting an axial force on the spinal rod and load ring sufficient to cause the gear-like teeth of the shaped post to shear through a least a portion of the receptacle to create an interdigitation of the gear-like teeth and receptacle to prevent further movement of the rod connector.

10. The method of claim 9, wherein the receptacle includes an annular lip overhang.

11. The method of claim 10, wherein gear-like teeth of the shaped post shear through one or more portions of the annular lip overhang.

12. The method of claim 9, wherein the lateral aperture is configured to allow the rod connector to pivot up to 15° in either direction while the setscrew is in the initial position.

13. The method of claim 9, wherein attaching the adjustable offset connector to the spinal rod includes:
- adjustably associating the rod connector and the anchor element by mating second end of the rod connector with the rod receiving element of the anchor element while the setscrew is in the first position;
- adjustably positioning the housing element in a desired position along the spinal rod while the setscrew is in the first position; and
- actuating the setscrew from the first position to the second position to effect compression of the offset connector by exerting an axial force on the spinal rod and load ring sufficient to cause the gear-like teeth of the shaped post to shear through a least a portion of the receptacle to create an interdigitation of the gear-like teeth and receptacle to prevent further movement of the rod connector.

* * * * *